United States Patent
Nakamura et al.

(10) Patent No.: US 7,833,160 B2
(45) Date of Patent: Nov. 16, 2010

(54) BLOOD VISCOSITY MEASUREMENT DEVICE

(75) Inventors: Takahiko Nakamura, Chiba (JP); Masataka Shinogi, Chiba (JP); Fumio Kimura, Chiba (JP); Mizuaki Suzuki, Chiba (JP)

(73) Assignee: Seiko Instruments Inc. (JP)

( * ) Notice: Subject to any disclaimer, the term of this patent is extended or adjusted under 35 U.S.C. 154(b) by 1256 days.

(21) Appl. No.: 11/341,757

(22) Filed: Jan. 27, 2006

(65) Prior Publication Data

US 2006/0184026 A1    Aug. 17, 2006

(30) Foreign Application Priority Data

Jan. 31, 2005    (JP) ............................. 2005-023391

(51) Int. Cl.
*A61B 8/00* (2006.01)
*A61B 5/00* (2006.01)

(52) U.S. Cl. ...................................... 600/438; 600/300

(58) Field of Classification Search ................. 600/438
See application file for complete search history.

(56) References Cited

U.S. PATENT DOCUMENTS

| | | | | |
|---|---|---|---|---|
| 3,735,756 | A | * | 5/1973 | Richards et al. ................. 601/2 |
| 4,671,295 | A | * | 6/1987 | Abrams et al. .............. 600/463 |
| 5,503,341 | A | * | 4/1996 | Kaneko et al. .............. 242/223 |
| 5,785,657 | A | * | 7/1998 | Breyer et al. ................. 600/454 |
| 5,791,345 | A | * | 8/1998 | Ishihara et al. .............. 600/368 |
| 7,207,939 | B2 | * | 4/2007 | Husher ........................ 600/370 |
| 2003/0032869 | A1 | * | 2/2003 | Muramatsu et al. .......... 600/300 |
| 2004/0236193 | A1 | * | 11/2004 | Sharf .......................... 600/302 |

* cited by examiner

*Primary Examiner*—Long V Le
*Assistant Examiner*—Hien Nguyen
(74) *Attorney, Agent, or Firm*—Adams & Wilks

(57) ABSTRACT

A blood viscosity measurement device has a flow rate calculating section that calculates a flow rate of blood flowing through a blood vessel of a living body. An inner diameter calculating section calculates an inner diameter of the blood vessel. A blood pressure data acquiring device acquires blood pressure data corresponding to a blood pressure of the blood vessel. A viscosity calculating section calculates a viscosity of the blood flowing through the blood vessel using each of the calculated flow rate, the calculated inner diameter, and the acquired blood pressure data.

4 Claims, 11 Drawing Sheets

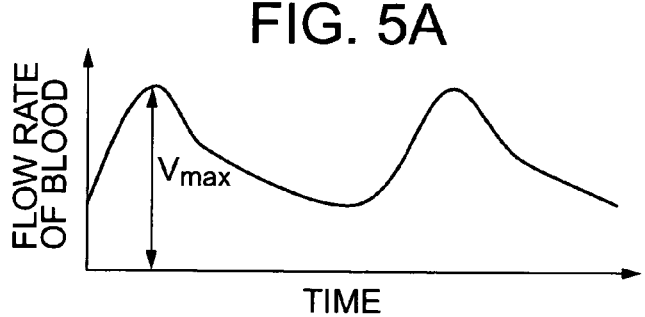
FIG. 5A
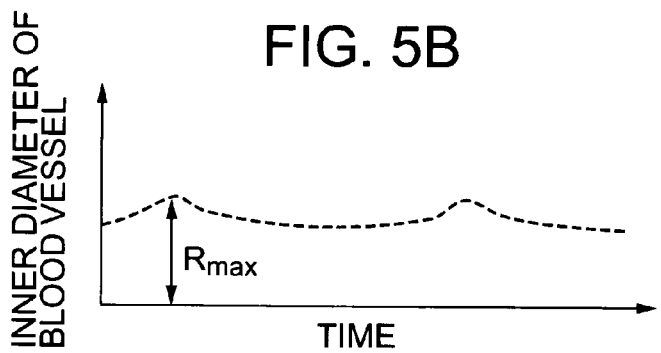
FIG. 5B
FIG. 6
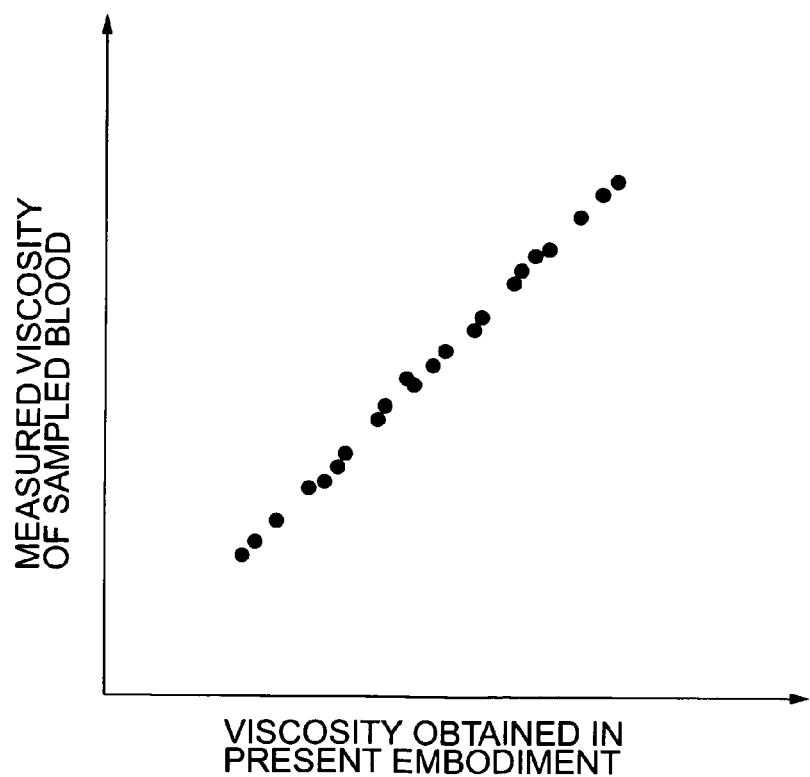

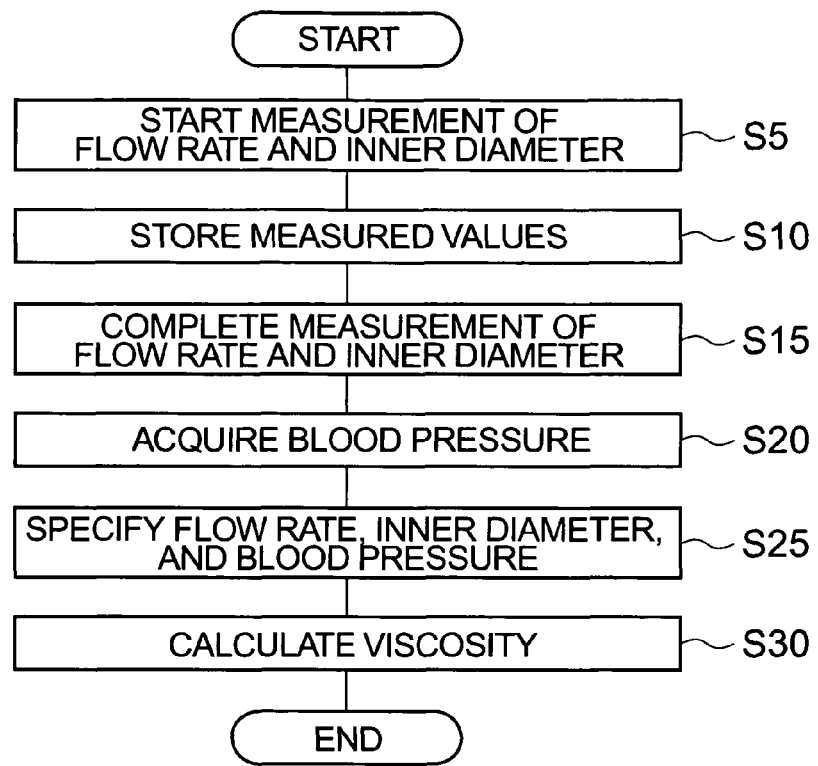
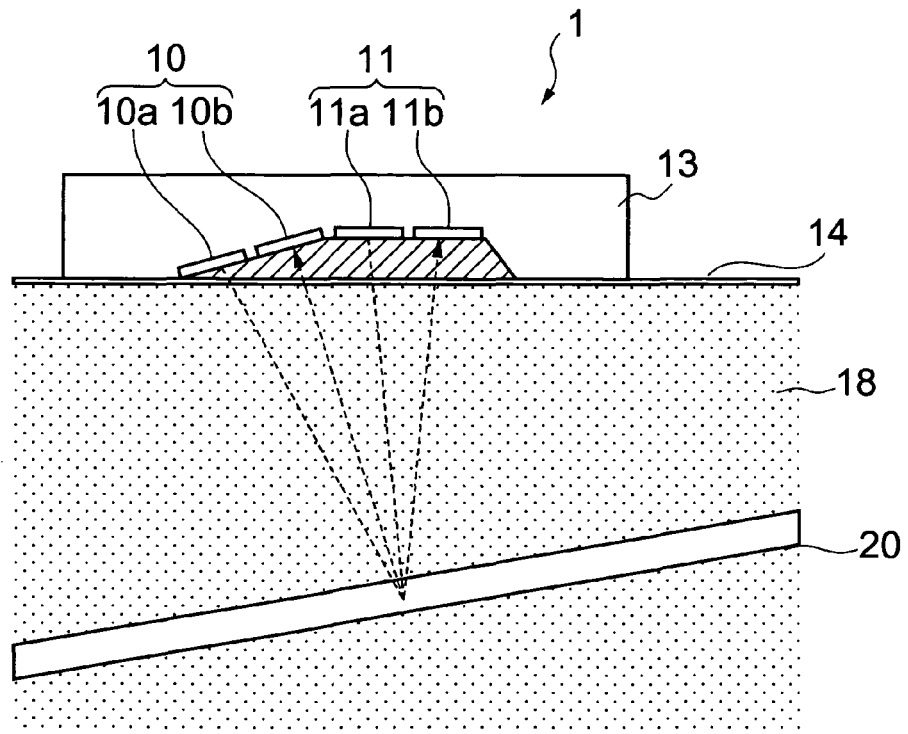

BLOOD VISCOSITY MEASUREMENT DEVICE

BACKGROUND OF THE INVENTION

1. Field of the Invention

The present invention relates to a blood viscosity measurement device and, more specifically, to a blood viscosity measurement device which non-invasively measures the viscosity of human blood.

2. Description of the Related Art

Inspection of a health condition has been broadly carried out by use of blood, but not only a numeric value of a blood component but also a flow of blood, that is, rheology (fluidity) of blood are important for correct inspection.

Moreover, one of indexes indicating the rheology of blood is blood viscosity. In general, the viscosity is referred to as "fluidity or adhesion of blood".

Heretofore, the viscosity of the blood sampled from human body has been measured with a measurement device, a viscometer or the like using a micro channel.

However, there are problems that qualification is required for performing a method involving the sampling of the blood and that it is difficult to check the flow of blood on a daily basis.

To solve the problems, in recent years, there has been proposed a device which measures a flow rate of blood non-invasively (i.e., without incising a living body or sticking a needle) in Japanese Patent Application Laid-Open No. 2003-204964 by the present applicant.

In this technology, the flow rate of the blood is non-invasively measured from a change amount of frequency of a reflected wave obtained by transmitting an ultrasonic wave to the blood. Since the blood flows in a certain direction, the ultrasonic wave reflected by the blood changes in frequency owing to Doppler effect. The flow rate of the blood can be obtained from the amount of this frequency change.

Moreover, in the technology of Japanese Patent Application Laid-Open No. 2003-204964, waves reflected in two different directions are received, and an angle (direction in which the blood flows) formed between a sensor and a blood vessel can be measured from the change amounts of the frequencies of these reflected waves. Furthermore, the flow rate is more correctly obtained in consideration of the measured angle. The viscosity can be estimated from the measured flow rate of the blood.

However, while carrying out investigations, it has been found that the flow rate of the blood depends on not only the viscosity of the blood but also a thickness of the blood vessel.

That is, the flow rate of even the blood having a low viscosity is reduced in a thin blood vessel, and the flow rate of even the blood having a high viscosity increases in a thick blood vessel.

Therefore, it has been newly found that not only the flow rate but also the thickness of the blood vessel need to be measured and considered in order to evaluate the viscosity of the blood more correctly.

An object of the present invention is to measure a flow rate of blood and a thickness of blood vessel in deciding a viscosity of blood.

SUMMARY OF THE INVENTION

To achieve the above-described object, according to the present invention, there is provided a blood viscosity measurement device comprising: flow rate measurement means for measuring a flow rate of blood flowing through a blood vessel; inner diameter measurement means for measuring an inner diameter of the blood vessel corresponding to the measured flow rate; and viscosity determining means for determining a viscosity of the blood by use of the measured flow rate and inner diameter (first constitution).

The first constitution may further comprise blood pressure acquiring means for acquiring a blood pressure of the blood vessel corresponding to the measured flow rate, and the viscosity determining means may determine the viscosity by use of the acquired blood pressure (second constitution).

In the second constitution, the viscosity determining means may determine the viscosity by use of maximum values of the measured flow rate, the inner diameter, and the acquired blood pressure (third constitution).

In the second or third constitution, the blood pressure acquiring means may acquire the measured blood pressure with a time difference from a time when the flow rate and the inner diameter are measured (fourth constitution).

The first to fourth constitutions may comprise: continuous wave transmitting means for transmitting continuous waves from the surface of a living body to the blood; and continuous wave receiving means for receiving a wave reflected by the blood among the transmitted continuous waves, and the flow rate measurement means calculates the flow rate by means of frequency change amounts of the received reflected waves having two directions (fifth constitution).

The first to fifth constitutions may comprise: pulse wave transmitting means for transmitting pulse waves from the surface of the living body to the blood vessel; and pulse wave receiving means for receiving a reflected wave reflected by the blood vessel among the transmitted pulse waves, and the inner diameter measurement means calculates the inner diameter of the blood vessel by use of the received pulse wave (sixth constitution).

The sixth constitution may comprise: a surge transmission element which transmits a surge from the living body surface into the living body; and element driving means for selectively generating the continuous wave and the pulse wave in the surge transmission element. When the element driving means switches the generations of the continuous wave and the pulse wave in the surge transmission element, the surge transmission element transmits the continuous wave to be used by the flow rate measurement means and the pulse wave to be used by the inner diameter measurement means (seventh constitution).

The second to seventh constitutions may comprise constant input accepting means for accepting input of a constant, and the viscosity determining means calculates the viscosity by means of an equation $\eta = k \times R^2 \times P/V$ wherein $\eta$ denotes the viscosity, V denotes the flow rate, R denotes the inner diameter, P denotes the blood pressure, and k denotes the constant (eighth constitution).

According to the present invention, the flow rate of the blood and the thickness of the blood vessel can be measured to determine the viscosity of the blood.

BRIEF DESCRIPTION OF THE DRAWINGS

FIG. 5 is a diagram showing a change of the flow rate of the blood with elapse of time;

FIG. 6 is an explanatory view of calibration of the blood viscosity measurement device;

FIG. 7 is a flowchart showing a procedure for measuring a viscosity with the blood viscosity measurement device;

FIG. 8 is a sectional view showing a structure of a sensor unit in a viscosity measurement device of Modification 1;

DESCRIPTION OF REFERENCE NUMERALS

Figure 1A:
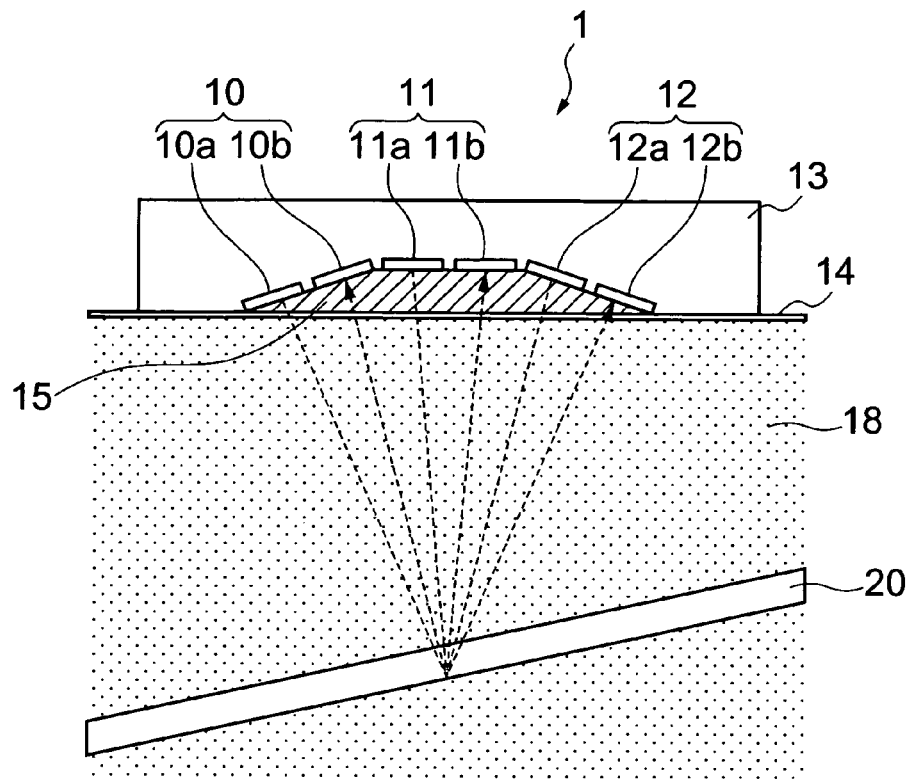
FIG. 1 is a diagram showing a sensor unit of a blood viscosity measurement device.

1 sensor unit,
2 circuit unit
3 calculation unit
4 output unit
10 transmitting/receiving element
11 transmitting/receiving element
12 transmitting/receiving element
13 base bottom section
14 skin
15 matching section
18 inside of living body
20 blood vessel

DETAILED DESCRIPTION OF THE PREFERRED EMBODIMENTS

Outline of Embodiment

In the present embodiment, a blood viscosity measurement device substitutes a flow rate of blood, a thickness of a blood vessel, and a blood pressure into a predetermined calculation formula to calculate a viscosity of the blood.

The flow rate of the blood is obtained from a change amount (Doppler shift) of frequency of a reflected continuous wave obtained by transmitting a continuous ultrasonic wave to a blood flow. A measurement method proposed in Japanese Patent Application Laid-Open No. 2003-204964 is utilized.

As to the thickness of the blood vessel, a pulse ultrasonic wave is transmitted to the blood vessel, and an inner diameter of the blood vessel is obtained from the pulse wave (echo) reflected by an inner wall of the blood vessel.

On the other hand, a value measured with a general blood pressure gauge or the like is utilized as the blood pressure.

The blood viscosity measurement device inputs, into a calculation formula described later, a maximum flow rate, a maximum inner diameter, and a maximum blood pressure among the values acquired as described above to calculate the viscosity of the blood.

Here, a reason why the maximum values are used is that the flow rate of the blood and the inner diameter of the blood vessel are maximized at a maximum blood pressure, and therefore the corresponding value can be acquired from these fluctuating values.

In the blood viscosity measurement device of the present embodiment, an ultrasonic wave transmitting/receiving element for measuring the blood flow rate and an ultrasonic wave transmitting/receiving element for measuring the inner diameter of the blood vessel can be incorporated in the same sensor, and the blood flow rate and the blood vessel inner diameter of the same portion can be measured simultaneously. This can improve a measurement precision of the blood viscosity.

Moreover, in the present embodiment, the blood viscosity measurement device can non-invasively measure the blood viscosity, and can be miniaturized. Therefore, a user can check a blood condition at home or in another place in daily life, and can readily take care of health.

Details of Embodiment

Figure 1B:
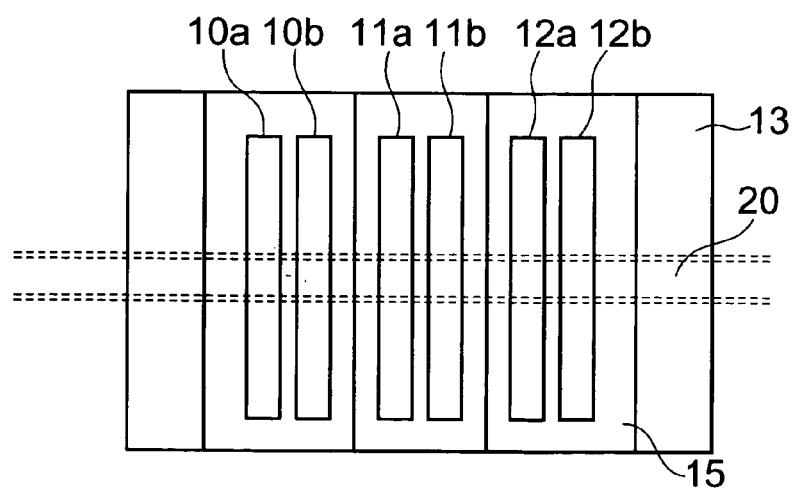

FIG. 1 shows a sensor unit of a blood viscosity measurement device, FIG. 1A shows a sectional view of the sensor unit, and FIG. 1B shows a bottom (face which comes in contact with human body) of the sensor unit.

Moreover, FIG. 1A shows skin 14, living body 18, and blood vessel 20 to which a sensor unit 1 has been attached.

The sensor unit 1 is a sensor which detects a flow rate of blood and a thickness (inner diameter) of the blood vessel, and is attached to, for example, human wrist, finger tip, arm or the like.

To be more specific, the sensor unit 1 is formed into, for example, a sack shape, so that the user's finger tip is inserted into the unit, or the sensor unit 1 is attached to a band to be attached to the wrist or arm.

Furthermore, the sensor unit 1 or a measurement system described later can be incorporated into a wristwatch. In this case, the wristwatch can be switched to a time measurement mode and a blood viscosity measurement mode, and the user can measure the viscosity in the blood viscosity measurement mode while the wristwatch is attached to the user's wrist as such.

The sensor unit 1 is constituted of: a transmitting and receiving element 10 including a transmitting element 10*a* and a receiving element 10*b*; a transmitting and receiving element 11 including a transmitting element 11*a* and a receiving element 11*b*; a transmitting and receiving element 12 including a transmitting element 12*a* and a receiving element 12*b*; a matching section 15 and the like. The transmitting elements 10*a*, 11*a*, and 12*a* constitute a surge transmitting element, and the receiving elements 10*b*, 11*b*, and 12*b* constitute a surge receiving element.

A base bottom section 13 is constituted of a single member made of a resin or the like, and holds the transmitting and receiving elements 10, 11, and 12 in predetermined positions in a face having such a direction as to come into the human body.

Each of the elements constituting the transmitting and receiving elements 10, 11, and 12 is constituted of a piezoelectric element, and are used in transmitting and receiving ultrasonic waves.

Among them, the transmitting and receiving elements 10 and 12 are used in measuring the flow rate of the blood, and the transmitting and receiving element 11 is used in measuring the inner diameter of the blood vessel.

To be more specific, in the transmitting and receiving element 10, the transmitting element 10a transmits a continuous ultrasonic wave (hereinafter referred to simply as the continuous wave) to the living body 18. This continuous wave is reflected by the blood flowing through the blood vessel 20, and is received by the receiving element 10b.

The frequency of the reflected continuous wave changes with Doppler effect due to the flow rate of the blood, and the flow rate of the blood can be obtained using a change amount (Doppler shift) of this frequency.

Similarly, in the transmitting and receiving element 12, the continuous wave transmitted from the transmitting element 12a is reflected by the blood flowing through the blood vessel 20, and received by the receiving element 12b.

As described later in detail, the transmitting and receiving elements 10 and 12 are fixed at predetermined angles in the base bottom section 13, and transmit the continuous waves to the blood vessel 20 in different directions. Accordingly, an angle formed by the sensor unit 1 and the blood vessel 20 can be calculated, and the flow rate of the blood can be calculated more correctly.

On the other hand, in the transmitting and receiving element 11, the transmitting element 11a transmits a pulse wave due to the ultrasonic wave (hereinafter referred to simply as the pulse wave) to the living body 18. This pulse wave is reflected by outer and inner walls of the blood vessel 20, and received by the receiving element 11b. The sensor unit 1 can detect the pulse wave reflected by the blood vessel 20 in this manner.

The matching section 15 is disposed on faces of the transmitting and receiving elements 10, 11, and 12 on an ultrasonic wave transmitting and receiving side.

The matching section 15 is constituted of an ultrasonic wave transmitting medium such as a resin, and constitutes an acoustic matching layer which adjusts impedances of the sensor unit 1 and the living body 18.

Specifically, the matching section 15 is preferably constituted of a medium having an approximately intermediate impedance between impedances of the transmitting and receiving elements 10 to 12 and the living body 18.

When changes of the impedance in a transmission path of the ultrasonic wave are reduced in this manner, the reflection of the ultrasonic wave can be reduced between the sensor unit 1 and the living body 18, and a transmission efficiency of the ultrasonic wave can be improved.

Next, there will be described a measurement principle of the flow rate of the blood flowing through the blood vessel 20 with reference to FIG. 2.

Figure 2A:
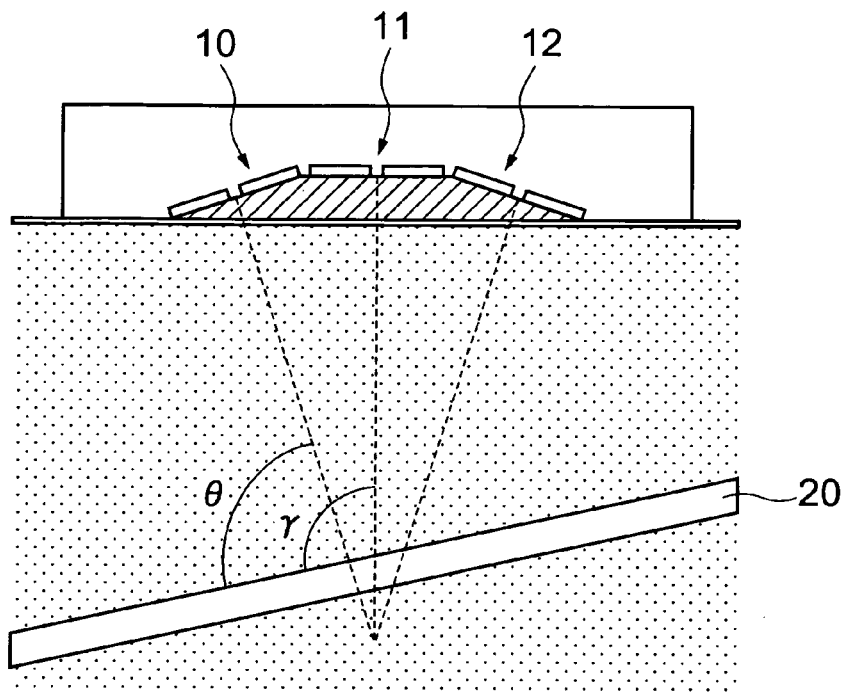
FIG. 2 is an explanatory view of a principle to measure a flow rate of blood.
Figure 2B:
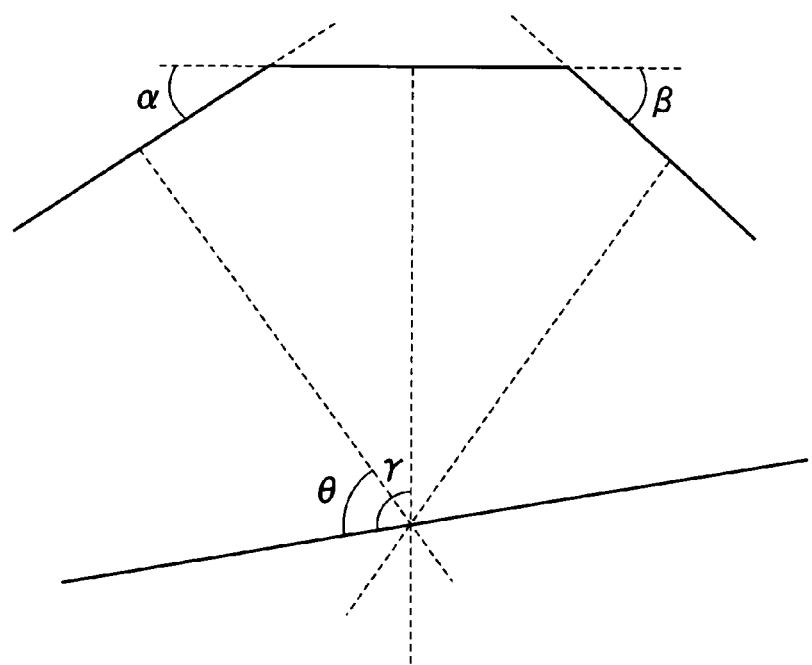

FIG. 2A shows a relation between an angle of the sensor unit 1 and that of the blood vessel 20 in FIG. 1, and FIG. 2B is a diagram showing extracted angle relations including an angle relation between the transmitting and receiving elements 10 and 12.

As shown, the transmitting and receiving elements 10, 11, and 12 are disposed to measure the flow rate of the blood and the inner diameter of the blood vessel 20 in the same portion of the blood vessel 20.

Moreover, it is assumed that an angle formed between a direction in which the transmitting and receiving element 11 transmits the pulse wave and the blood vessel 20 is γ, and an angle formed between a direction in which the transmitting and receiving element 10 transmits the continuous wave and the blood vessel 20 is θ.

It is also assumed that angles formed by the transmitting and receiving elements 10 and 12 with respect to the surface of the living body 18 are α and β, respectively.

When the angles are set as described above, and it is assumed that a change amount of frequency detected by the transmitting and receiving element 10 is Δf1 and that a change amount of frequency detected by the transmitting and receiving element 12 is Δf2, these change amounts are given by the following equations (1) and (2):

$$\Delta f1 = 2 \times v \times \cos\theta \times F/c \quad (1); \text{ and}$$

$$\Delta f2 = 2 \times v \times \cos(\theta+\alpha+\beta) \times F/c \quad (2).$$

In the above equations (1) and (2), c denotes an acoustic velocity in the living body 18, which is about 1530 [m/s]. Moreover, F denotes the frequency of the ultrasonic wave transmitted to the inside of the living body 18, and v denotes the flow rate of the blood. From the equations (1) and (2), θ is represented by the following equation (3).

$$\tan\theta = (\Delta f2/\Delta f1 - \cos(\theta+\alpha+\beta))/c \quad (3)$$

When θ is obtained once, this can be applied to the equation (1) to obtain the flow rate v of the blood.

Moreover, γ can be obtained by the following equation (4), and this is used in calculating the inner diameter of the blood vessel.

$$\gamma = \theta + \alpha \quad (4)$$

As described above, the flow rate v of the blood vessel 20 and the angles θ and γ (directions in the living body 18) formed between the blood vessel 20 and the sensor unit 1 can be calculated from the change amount of the frequency detected by the transmitting and receiving elements 10 and 12.

Figure 3:
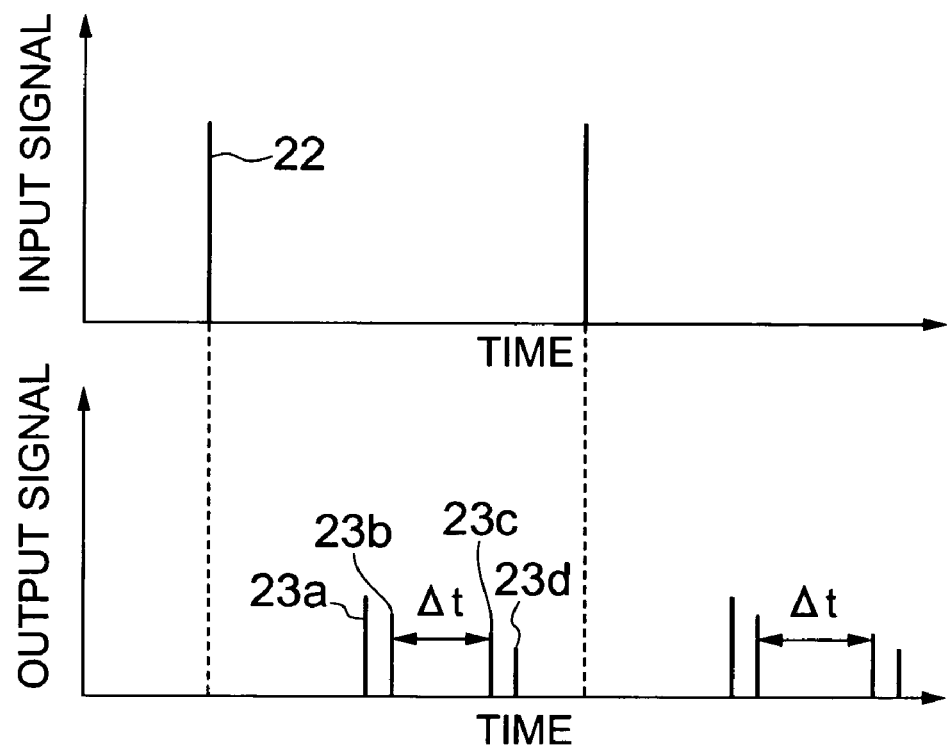
FIG. 3 is an explanatory view of a principle to measure an inner diameter of a blood vessel.

Next, there will be described a principle to measure the inner diameter of the blood vessel with reference to FIG. 3.

Here, it is assumed that a positional relation between the sensor unit 1 and the blood vessel 20 is as shown in FIG. 2A.

FIG. 3A shows a pulse wave transmitted by the transmitting element 11a, and FIG. 3B shows a reflected pulse wave received by the receiving element 11b. In either drawing, the ordinate indicates a size of pulse by means of a voltage, and the abscissa indicates time. Time axes of FIGS. 3A and 3B are matched.

When the transmitting element 11a transmits a pulse wave 22 to the inside of the living body 18, reflected pulse waves 23a to 23d reflected by the blood vessel 20 are received by the receiving element 11b.

The pulse waves are reflected by the outer and inner walls of a portion on a sensor unit 1 side of the blood vessel 20, and those of a portion of the blood vessel facing this portion, and they are received in this order. Since the blood vessel 20 has a tubular shape, the reflected pulse wave reflected by a side face of the blood vessel is diffused in the living body 18.

Therefore, it is seen that the reflected pulse wave 23a is reflected by a portion of the outer wall of the blood vessel 20 close to the skin 14, the reflected pulse wave 23b is reflected by a portion of the inner wall of the blood vessel 20 close to the skin 14, the reflected pulse wave 23c is reflected by a portion of the inner wall of the blood vessel 20 distant from the skin 14, and the reflected pulse wave 23d is reflected by a portion of the blood vessel 20 distant from the skin 14.

As described above, the reflected pulse waves 23b and 23c are reflected from the inner wall of the blood vessel 20. Assuming that a time difference from a time when reflected pulse 23b is received until the pulse wave 23c is received is Δt, the inner diameter R is represented by the following equation (5):

$$R = c \times \Delta t \times \sin \gamma / 2 \qquad (5),$$

wherein γ is obtained by the equation (4), and Δt is measured to thereby calculate the inner diameter of the blood vessel 20.

Next, a system constitution of the blood viscosity measurement device will be described with reference to a block diagram of FIG. 4.

Figure 4:
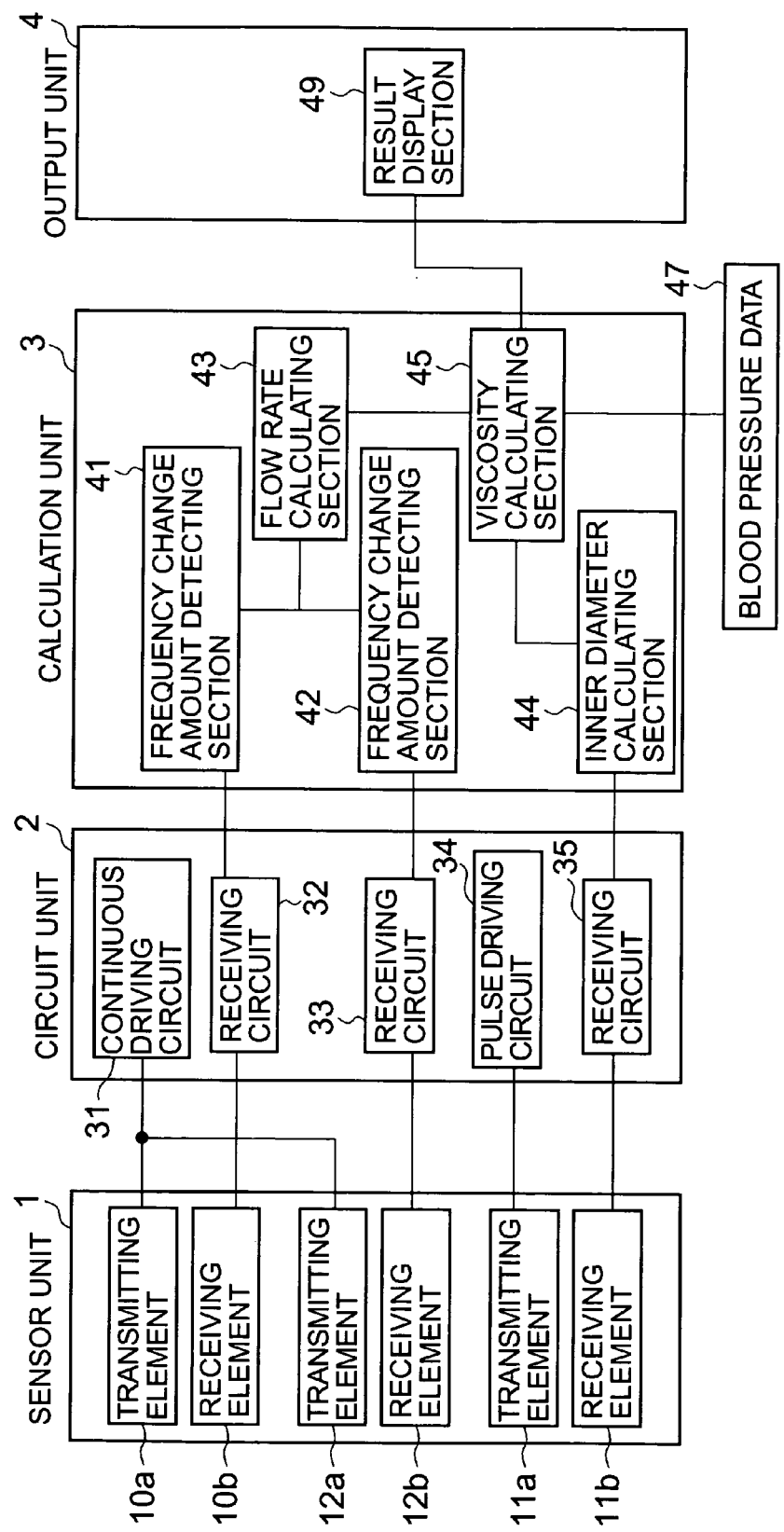
FIG. 4 is a block diagram showing a constitution of the blood viscosity measurement device.

As shown in FIG. 4, the blood viscosity measurement device of the present embodiment is constituted of the sensor unit 1, a circuit unit 2, a calculation unit 3, and an output unit 4.

The circuit unit 2 is a functional unit which drives the sensor unit 1 and which transmits the signal detected by the sensor unit 1 to the calculation unit 3, and is constituted of a continuous driving circuit 31, a receiving circuit 32, a receiving circuit 33, a pulse driving circuit 34, a receiving circuit 35 and the like.

The continuous driving circuit 31 is connected to the transmitting elements 10a and 12a, and drives these elements to generate the continuous wave. The frequency of the continuous wave driven by the continuous driving circuit 31 is generally about 10 to 20 [MHz], and set to 15 [MHz] as an example here. The continuous driving circuit 31 constitutes continuous wave transmitting means.

When the frequency of the ultrasonic wave heightens, a resolution thereof increases, but a distance by which the wave permeates the living body 18 shortens. Conversely, when the frequency lowers, the distance by which the wave permeates the living body 18 lengthens, but the resolution lowers. Therefore, an appropriate frequency is selected in consideration of these properties.

The receiving circuit 32 is connected to the receiving element 10b, and receives the reflected continuous wave of the continuous wave output from the transmitting element 10a to output the wave to the calculation unit 3.

The receiving circuit 33 is connected to the receiving element 12b, and receives the reflected continuous wave of the continuous wave output from the transmitting element 12a to output the wave to the calculation unit 3.

The receiving circuits 32 and 33 constitute continuous wave receiving means.

The pulse driving circuit 34 is connected to the transmitting element 11a, and drives the element to generate the pulse wave. An interval of the pulse generated by the pulse driving circuit 34 is set to about 1 [msec]. The pulse driving circuit 34 constitutes pulse transmitting means.

The pulse driving circuit 35 is connected to the receiving element 11b, and receives the reflected pulse wave of the pulse wave output from the transmitting element 11a to output the wave to the calculation unit 3. The receiving circuit 35 constitutes pulse receiving means.

A time interval from a time when the transmitting element 11a generates the pulse until the reflected pulse returns is generally about 20 to 30 [μsec]. When a pulse generation interval is set to be sufficiently longer than this interval, the next pulse can be prevented from being generated before the reflected pulse wave is received. Consequently, it is possible to identify a time when the pulse wave from which the received reflected pulse wave is derived is transmitted.

It is to be noted that although not shown, filters are disposed between the receiving elements 10b to 12b and the circuit unit 2, respectively, and the reflected wave obtained from the transmitting element other than the corresponding transmitting element is prevented from being received.

The calculation unit 3 is constituted of frequency change amount detecting sections 41, 42, a flow rate output section 43, an inner diameter calculating section 44, a viscosity calculating section 45 and the like.

The frequency change amount detecting section 41 is connected to the receiving circuit 32, and acquires, from the receiving circuit 32, the frequency of the reflected continuous wave detected by the receiving element 10b.

Moreover, the frequency change amount detecting section 41 compares the frequency of the continuous wave transmitted from the transmitting element 10a to the living body 18 with that of the reflected continuous wave acquired from the receiving circuit 32, and detects the change amount of the frequency in the transmitting and receiving element 10.

The frequency change amount detecting section 41 may store the frequency of the continuous wave transmitted from the transmitting element 10a, or acquire the frequency from the continuous driving circuit 31.

The frequency change amount detecting section 42 is connected to the receiving circuit 33, and acquires, from the receiving circuit 33, the frequency of the reflected continuous wave detected by the receiving element 12b.

Moreover, the section detects the change amount of the frequency in the transmitting and receiving element 12 in the same manner as in the frequency change amount detecting section 41.

The flow rate output section 43 acquires, from the frequency change amount detecting section 41, the change amount of the frequency in the transmitting and receiving element 10, and acquires, from the frequency change amount detecting section 42, the change amount of the frequency in the transmitting and receiving element 12.

Moreover, the flow rate output section 43 substitutes these values into the equations (3) and (4) to calculate v (flow rate of blood) of the blood flow, θ, and γ. The flow rate output section 43 constitutes the flow rate measurement means.

The inner diameter calculating section 44 is connected to the receiving circuit 35, and acquires the reflected pulse wave from the receiving circuit 35 to calculate the inner diameter of the blood vessel 20.

The inner diameter calculating section 44 detects Δt from the data output from the receiving circuit 35, and substitutes this value into the equation (5) to calculate the inner diameter. The angle γ required for the inner diameter calculation is acquired from the flow rate output section 43. The inner diameter calculating section 44 constitutes inner diameter measurement means.

The viscosity calculating section 45 acquires the flow rate of the blood from the flow rate output section 43, acquires the inner diameter of the blood vessel 20 from the inner diameter calculating section 44, and acquires blood pressure data 47 from the outside to calculate the viscosity of the blood by use of these data. The viscosity calculating section 45 constitutes viscosity determining means.

As to the blood pressure data 47, a user inputs the value measured using a general blood pressure gauge. Therefore, the calculation unit 3 can be provided with a user interface such as a keyboard for inputting a numeric value. Alternatively, the calculation unit may be connected to the blood pressure gauge via the interface.

It is to be noted that in the present embodiment, the viscosity is calculated using a maximum blood pressure as described later, and at least the maximum blood pressure is input as the blood pressure data 47. The calculation unit 3 is provided with blood pressure acquiring means in this manner.

Here, there will be described a principle on which the viscosity calculating section 45 calculates the viscosity of the blood.

FIG. 5A is a diagram showing a change of the flow rate acquired by the viscosity calculating section 45 from the flow rate output section 43 with elapse of time. It is to be noted that the ordinate shows the flow rate, and the abscissa shows the time.

As shown in the drawing, the flow rate detected by the flow rate output section 43 vertically pulsates along with heartbeat.

The viscosity calculating section 45 acquires maximum value Vmax of the flow rate from flow rate data acquired from the flow rate output section 43. The maximum value of the flow rate for acquiring Vmax may be any of the maximum values detected every heartbeat. It is to be noted that the maximum flow rate is extracted from the flow rate data every heartbeat, and averaged to obtain Vmax.

FIG. 5B is a diagram showing a change of the inner diameter acquired by the viscosity calculating section 45 from the inner diameter calculating section 44 with elapse of time. It is to be noted that the ordinate shows the flow rate, and the abscissa shows the time. Furthermore, a time axis is matched with that of FIG. 5A. The inner diameter of the blood vessel 20 fluctuates with the heartbeat. The change of the blood flow is associated with that of the inner diameter in such a manner that the inner diameter is maximize when the blood flow is maximized.

The viscosity calculating section 45 acquires a maximum value Rmax of the inner diameter from inner diameter data acquired from the inner diameter calculating section 44. It is to be noted that the maximum value of the inner diameter for acquiring Rmax is a value at a time which agrees with that of Vmax of FIG. 5A.

Accordingly, the viscosity calculating section 45 can acquire the maximum value Rmax of the inner diameter corresponding to the maximum value Vmax of the blood flow.

It is to be noted that the maximum value may be extracted as Rmax from the inner diameter data and averaged for use.

A time required for measuring the viscosity is about ten seconds, and a condition of the blood flow does not change largely for the time. Therefore, the inner diameter Rmax of the blood vessel does not have to be set to the value at the same time as that of Vmax, and another inner diameter maximum value may be set to Rmax.

It is supposed that the blood pressure at a time when the blood flow rate is Vmax and the inner diameter is Rmax is a maximum blood pressure. Therefore, the viscosity calculating section 45 acquires the maximum blood pressure from the blood pressure data 47 as a blood pressure Pmax at a time when Vmax and Rmax are acquired.

It is to be noted that in the present embodiment, the flow rate and the inner diameter are measured separately from the measuring of the blood pressure. Therefore, the changes of the flow rate and the inner diameter due to the blood pressure measurement do not have to be considered.

In the measuring of the blood pressure, changes are generated in the blood flow by oppressing arms. Therefore, the blood pressure is preferably measured after measuring the flow rate and the inner diameter.

The viscosity calculating section 45 acquires Vmax, Rmax, and Pmax in this manner, and substitutes the values into the following equation (6) to calculate viscosity η of the blood.

$$\eta = k \times (Rmax)^2 \times Pmax / Vmax \quad (6),$$

wherein k denotes a constant.

It is to be noted that the maximum values of the flow rate, the inner diameter, and the blood pressure are used in viscosity calculation of the equation (6). When the maximum values are used, it is easy to acquire corresponding values of the flow rate, inner diameter, and blood pressure. That is, it is supposed that when the flow rate is maximized, the inner diameter and the blood pressure are maximized. Therefore, the inner diameter and the blood pressure at a time when the flow rate reaches its maximum value may be set as the maximum inner diameter and the maximum blood pressure, respectively.

The equation (6) is a generally established equation without depending on these maximum values. When the inner diameter and the blood pressure at a certain flow rate are known, they may be substituted into the equation (6) to obtain the viscosity.

Here, the equation (6) is estimated from the Hagen Poiseuille equation, and obtained by the present inventors.

The Hagen Poiseuille equation is an equation to obtain the flow rate in a case where Newton fluid flows through a tube having a certain radius R, and is given by the following equation (7):

$$V = R^2 \times (P1-P2)/(4 \times \eta \times l) \quad (7),$$

wherein P1 denotes a pressure of the fluid at a certain point on an upstream side, P2 denotes a pressure of the fluid at a certain point on a downstream side, l denotes a distance between two points, and η denotes a viscosity.

According to the Hagen Poiseuille equation (7), the viscosity of the fluid is proportional to a sectional area of a transport tube and the pressure of the fluid, and is inversely proportional to the flow rate. Therefore, the equation (6) to obtain the viscosity has been found.

The constant k introduced by the equation (6) can be used in calibrating the measured value of the viscosity η.

That is, when the user sets k as described later with reference to FIG. 6, the value of the viscosity measured by a medical institution or the like can be matched with the value measured by the blood viscosity measurement device of the present invention. This respect will be described later in more detail.

Moreover, the viscosity calculating section 45 outputs the value η of the viscosity calculated by the equation (6) to the output unit 4.

The calculation unit 3 is provided with hardware such as a central processing unit (CPU), a read only memory (ROM), a random access memory (RAM), and an electrically erasable and programmable ROM (EEPROM) in order to calculate the viscosity η as described above.

The CPU is a central processing unit, and performs various types of calculation processing, controls the whole calculation unit 3, and controls the transmission/reception of the data with respect to the circuit unit 2 or the output unit 4 in accordance with programs stored in the ROM, the RAM, the EEPROM and the like.

The ROM is a read-only storage medium in which a parameter, a program and the like for allowing the calculation unit 3 to function are basically stored. The CPU initializes the blood viscosity measurement device by use of the parameter, program and the like at a time when the device is started.

The RAM is a storage medium which is readable and writable as needed. The RAM provides an area for storing the data acquired from the receiving circuits 32 and 33 and the inner diameter calculating section 44, for example, when the CPU calculates the viscosity of the blood, or provides a working area, when the viscosity is calculated using the data stored in these areas.

The EEPROM is a ROM in which the data can be rewritten or deleted later by an electric operation.

In the present embodiment, in addition to an operating system which is a basic program for operating the calculation unit 3, a blood viscosity calculation program for calculating the viscosity of the blood and the like, a value of the constant k for use in the equation (6) is stored in the EEPROM.

The CPU executes a blood viscosity program to thereby constitute, as software, functional sections of the frequency change amount detecting section 41, the frequency change amount detecting section 42, the inner diameter calculating section 44, the flow rate output section 43, the viscosity calculating section 45 and the like.

Moreover, the calculation unit 3 is provided with a large-capacity storage medium such as a hard disk, and accumulates user's daily viscosities.

Furthermore, the calculation unit 3 is provided with an input/output interface, and outputs viscosity data to an external computer or read the data or the program from the outside.

In addition, the calculation unit 3 is provided with a storage medium driving device for driving an external storage medium constituted of a flexible disk, a magnetic optical disk, a semiconductor memory and the like, so that the viscosity data is written into these external storage mediums, or the data or the program written in the external storage medium is read.

The above-described constitution is one example of a hardware constitution of the calculation unit 3, and does not limit the constitution of the calculation unit 3. Any constitution may be used as long as the frequency change amount detecting section 41 to the viscosity calculating section 45 are formed.

Moreover, an output of the sensor unit 1 is analog data, and data processed by the calculation unit 3 is digital data. Therefore, the analog data needs to be sampled and converted into the digital data in a certain stage. This may be performed by the circuit unit 2 or the calculation unit 3.

Next, the output unit 4 will be described. The output unit 4 is provided with a result display section 49, and the viscosity $\eta$ output from the viscosity calculating section 45 is displayed.

The display device is constituted of, for example, a liquid crystal display, a plasma display, a CRT display and the like, and a value of $\eta$ is displayed in a numeric value. The value of $\eta$ may be displayed using a graph, another diagram, a symbol or the like.

Next, one example of calibration of the constant k will be described by use of a graph of FIG. 6.

The ordinate of FIG. 6 indicates a size of a value of viscosity measured with another blood viscosity measurement device installed in the medical institution or the like, and the abscissa indicates a size of a value of viscosity measured with the present blood viscosity measurement device.

Moreover, on the graph, there are plotted values measured with both of the devices with respect to samples of fluids having different viscosities.

Points are plotted linearly in this manner. Therefore, the value of the constant k can be appropriately set to perform the calibration so that the values measured with both of the devices agree with each other.

Therefore, for example, the user measures the viscosity with the blood viscosity measurement device installed in the medical institution regularly visited by the user, and with the present blood viscosity measurement device. When the constant k is set and stored so that both of the values are equal, the viscosity can be measured with the only present blood viscosity measurement device from that time.

There are several methods of measuring the viscosity of the blood, and the measured value sometimes differs with the measurement method and the blood viscosity measurement device.

Therefore, the device is provided with a function of calibrating the measured value in this manner. Accordingly, the present blood viscosity measurement device can be adjusted so as to correspond to a specific blood viscosity measurement device, and the viscosity of the blood can be measured at home on the same constitutions as those of the regularly visited hospital.

It is to be noted that a designed and determined default value is stored at a time when the present blood viscosity measurement device is shipped.

Next, there will be described a procedure of viscosity measurement by the present blood viscosity measurement device with reference to a flowchart of FIG. 7.

First, the calculation unit 3 drives the sensor unit 1 to start measurement of the flow rate with the transmitting and receiving elements 10 and 12 and measurement of the inner diameter with the transmitting and receiving element 11 (step 5).

Next, the circuit unit 2 receives these measured values from the sensor unit 1, and outputs them to the calculation unit 3. The calculation unit 3 receives these measured values from the circuit unit 2, and stores them in a storage device such as the RAM (step 10).

This processing to store the measured values in a storage device is continued while the measured values required for the measurement of the viscosity are accumulated (e.g., about ten seconds), and completed (step 15).

Next, the calculation unit 3 accepts the input of the blood pressure value from the user, and acquires and stores the value (step 20).

Next, the calculation unit 3 specifies the maximum blood pressure value, the maximum flow rate, and the maximum inner diameter from the stored measured values (step 25), and calculates the viscosity by use of these measured values (step 30). The calculated viscosity is output from the output unit 4.

The present embodiment has been described above. The following effects can be obtained in the present embodiment.

(1) The viscosity of the blood can be non-invasively measured.

(2) Since the viscosity is obtained in consideration of the flow rate of the blood and the thickness (inner diameter) of the blood vessel, the viscosity can be measured more correctly.

(3) Since the maximum values of the blood pressure, the flow rate, and the inner diameter are specified to measure the viscosity, the viscosity can be calculated using the corresponding values of the blood pressure, the flow rate, and the inner diameter.

(4) The constant k can be set to calibrate the measured value.

(5) Since any of the sensor unit 1, the circuit unit 2, the calculation unit 3, and the output unit 4 can be miniaturized, they can be installed at home so that the user can readily measure the viscosity. The device may be attached to the wrist watch to measure the viscosity as needed.

It is to be noted that in the present embodiment, the viscosity is calculated using the flow rate, the inner diameter, and the pressure as parameters, but the calibration can be performed so as to obtain a rough viscosity value by use of the flow rate and the inner diameter without using the pressure. In this case, for example, Pmax can be included in k in the equation (6) to thereby calculate the viscosity.

In this case, an error as much as a blood pressure fluctuation is generated in the measured value of the viscosity, but the blood pressure does not largely fluctuate in a short time. Therefore, the device is effective in a case where transition of the viscosity is roughly measured over the short time.

Moreover, in the present embodiment, the ultrasonic wave is used in measuring the flow rate of the blood or the inner diameter of the blood vessel, but the surge for the measurement is not limited to the ultrasonic wave, and the measurement may be performed by use of, for example, another surge of laser or the like.

(Modification 1)

Next, Modification 1 of the present embodiment will be described.

FIG. 8 is a sectional view showing a structure of a sensor section of a blood viscosity measurement device in Modification 1.

In Modification 1, a continuous wave and a pulse wave are selectively generated by a transmitting and receiving element 11, and the transmitting and receiving element 11 is provided with both of a function of measuring a flow rate of blood and a function of measuring an inner diameter of a blood vessel.

It is to be noted that in the following description, functional sections corresponding to those of the above-described embodiment are denoted with the same reference numerals, and description of the same operation as that of the embodiment is simplified or omitted.

A transmitting and receiving element 10 sends a continuous ultrasonic wave to a living body 18 in the same manner as in the embodiment, and a change of a frequency of the blood flowing through a blood vessel 20 is continuously measured over a measurement time.

When the measurement is started, the transmitting and receiving element 11 sends the continuous wave to the living body 18 for a certain time, and thereafter sends the pulse wave.

On the basis of the continuous wave sent from the transmitting and receiving element 11 for a certain time, and the continuous wave transmitted from the transmitting and receiving element 10, an angle θ of the blood vessel 20 which is required for the measurement of the blood flow is calculated in accordance with the equation (3). After θ is once obtained, a detected value in the transmitting and receiving element 10 can be applied to the equation (1) to calculate the flow rate of the blood.

Moreover, the inner diameter of the blood vessel 20 can be measured by means of the pulse wave subsequently sent after the continuous wave from the transmitting and receiving element 11.

The measured value required for the calculation of the angle θ of the blood vessel 20 can be acquired in this manner while the transmitting and receiving element 11 sends the continuous wave. Therefore, the viscosity can be thereafter measured by means of the pulse wave send from the transmitting and receiving element 11 and the continuous wave sent from the transmitting and receiving element 10.

Figure 9:
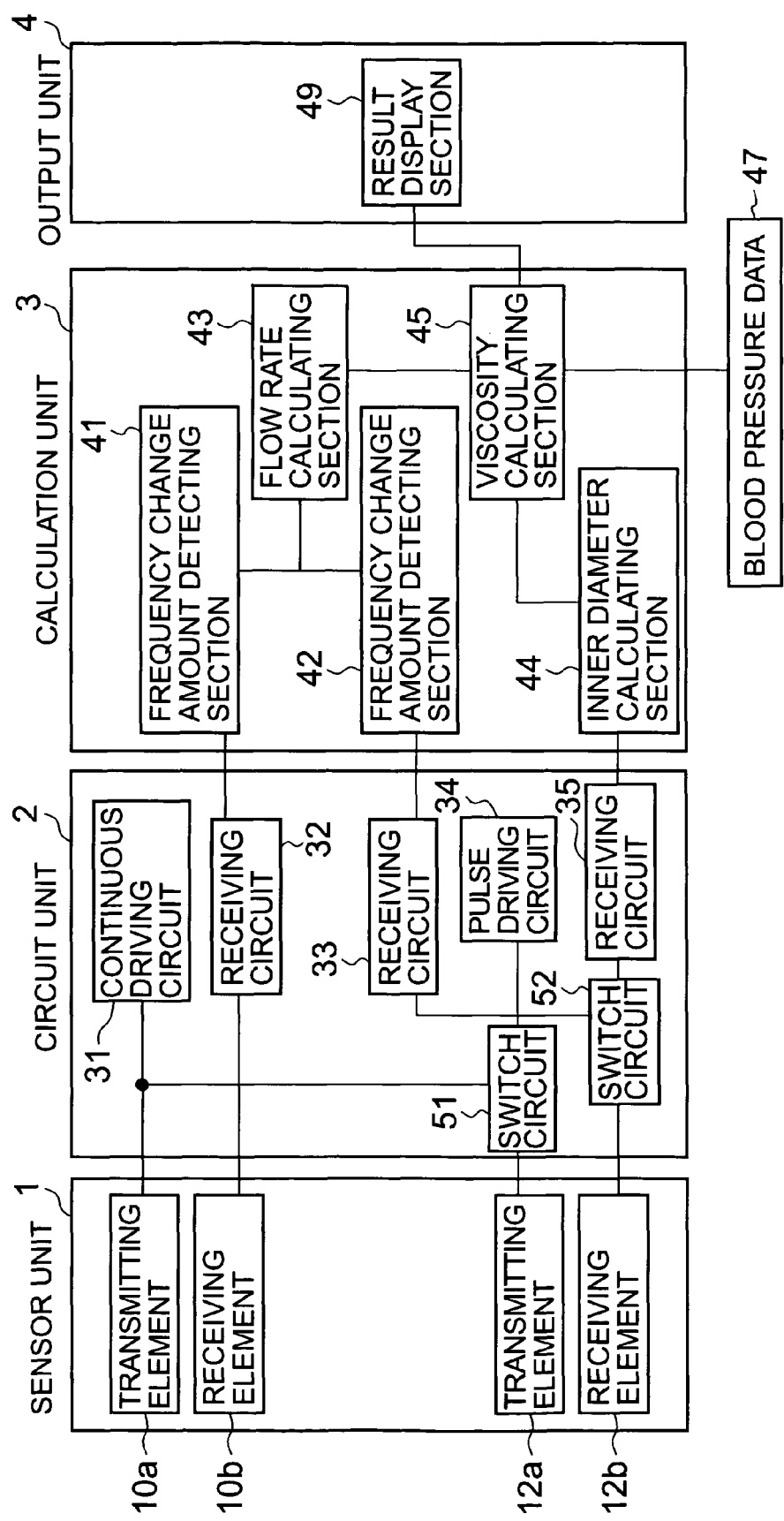
FIG. 9 is a block diagram showing a constitution of the blood viscosity measurement device of Modification 1.

Next, there will be described a system constitution of the blood viscosity measurement device of Modification 1 with reference to a block diagram of FIG. 9.

The blood viscosity measurement device of Modification 1 is constituted of a sensor unit 1, a circuit unit 2, a calculation unit 3, and an output unit 4.

A continuous driving circuit 31 is connected to a transmitting element 10a, and is connected to a transmitting element 12a via a switch circuit 51.

Moreover, a pulse driving circuit 34 is connected to the transmitting element 12a via the switch circuit 51.

The switch circuit 51 is a circuit which selects a circuit to drive the transmitting element 12a. The switch circuit 51 can be switched to drive the transmitting element 12a with the continuous driving circuit 31 or the pulse driving circuit 34.

Moreover, when the transmitting element 12a is driven by the continuous driving circuit 31, the continuous wave is transmitted to the living body 18. When the element is driven by the pulse driving circuit 34, the pulse wave is transmitted.

As described above, the continuous driving circuit 31, the pulse driving circuit 34, and the switch circuit 51 constitute element driving means for selectively generating the continuous wave and the pulse wave.

A receiving circuit 33 is connected to a receiving element 12b via a switch circuit 52, and a receiving circuit 35 is also connected to the receiving element 12b via the switch circuit 52.

The switch circuit 52 is a circuit which selects the receiving circuit to receive a reflected wave detected by the receiving element 12b. The switch circuit 52 can be switched so that the receiving circuit 33 or 35 receives the reflected wave.

The circuit unit 2 synchronously switches the switch circuits 51 and 52. When the transmitting element 12a is driven by the continuous driving circuit 31, the receiving element 12b is connected to the receiving circuit 33. When the transmitting element 12a is driven by the pulse driving circuit 34, the receiving element 12b is connected to the receiving circuit 35.

Therefore, when the transmitting element 12a transmits the continuous wave, the reflected continuous wave received by the receiving element 12b is output to a frequency change amount detecting section 42 via the receiving circuit 33. When the transmitting element 12a transmits the pulse wave, a reflected pulse wave received by the receiving element 12b is output to an inner diameter calculating section 44 via the receiving circuit 35.

In this manner, the circuit unit 2 switches the transmitting and receiving element 12 to a continuous wave mode and a pulse wave mode, and the element is used in measuring both of the flow rate of the blood and the inner diameter of the blood vessel.

Figure 10:
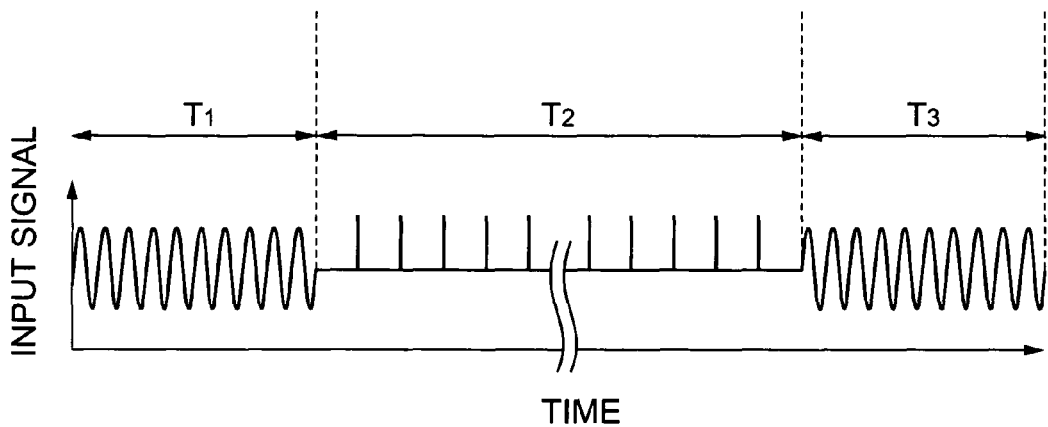
FIG. 10 is an explanatory view of switching of an ultrasonic wave mode in Modification 1.

FIG. 10 is an explanatory view of the switching of the mode of the ultrasonic wave transmitted from the transmitting and receiving element 12 during the measurement of the viscosity.

In FIG. 10, the ordinate indicates a size of an output of a transmitted wave in terms of a voltage, and the abscissa indicates time.

As shown in FIG. 10, the circuit unit 2 of Modification 1 drives the transmitting and receiving element 12 in the continuous wave mode for time T1 from a time when the measurement is started. Thereafter, the element is driven in a pulse wave mode for time T2. Moreover, the mode is switched again to the continuous wave mode, and continued for time T3.

In Modification 1, as one example, T1 and T3 are set to about one second, and T2 is set to about ten seconds. A pulse wave interval is about 0.1 [msec] in the pulse wave mode.

It is to be noted that although not shown, the transmitting and receiving element 10 transmits the continuous wave from the start of the measurement until the end of the measurement.

The blood viscosity measurement device of Modification 1 calculates θ by use of signals from the transmitting and receiving elements 10 and 12 for T1 after the end of the measurement.

Moreover, the blood viscosity measurement device of Modification 1 measures the flow rate of the blood in response to the signal from the transmitting and receiving element 10 for time T2, and measures the inner diameter of the blood vessel 20 in response to the signal from the transmitting and receiving element 12.

Moreover, the blood viscosity measurement device of Modification 1 measures θ again for time T3, and confirms whether or not the value θ agrees with the value measured in the time T1.

When θ agrees with the value, the calculation unit 3 of Modification 1 calculates the viscosity by use of θ. When θ does not agree, the viscosity is calculated using an average value of θ, or θ is measured again.

In Modification 1 described above, the sensor unit 1 can be provided with only two transmitting and receiving elements (transmitting and receiving elements 10 and 12).

Therefore, manufacturing costs of the blood viscosity measurement device can be reduced.

(Modification 2)

Next, Modification 2 of the present embodiment will be described.

Figure 11:
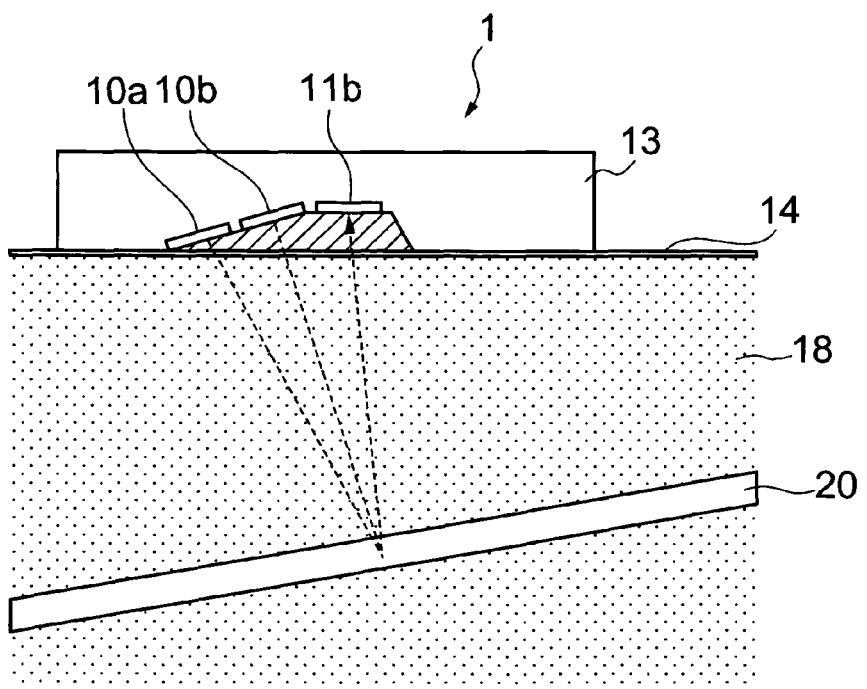
FIG. 11 is a sectional view showing a structure of a sensor unit in a viscosity measurement device of Modification 2.

FIG. 11 is a sectional view showing a structure of a sensor unit of a blood viscosity measurement device in Modification 2.

Modification 2 is similar to Modification 1 in that a transmitting element 11a is driven in a continuous wave mode and a pulse wave mode. However, a transmitting element 10a is not disposed, and transmission of a continuous wave from the transmitting element 10a is not performed.

The transmitting element 11a alternately transmits the continuous wave and a pulse wave to a living body 18, for example, every 0.1 [msec].

In the blood viscosity measurement device of Modification 2, when the transmitting element 11a transmits the continuous wave, the continuous wave reflected by a blood flow is received by receiving elements 10b, 11b, and a flow rate of blood is obtained from change amounts of frequencies of these received reflected continuous waves.

In the blood viscosity measurement device of Modification 2, when the transmitting element 11a transmits the pulse wave, the pulse wave reflected by a blood vessel 20 is received by the receiving element 11b, and an inner diameter of the blood vessel 20 is measured using this wave. It is to be noted that the transmitting element 11a may receive the reflected pulse wave to thereby measure the inner diameter of the blood vessel 20.

Figure 12:
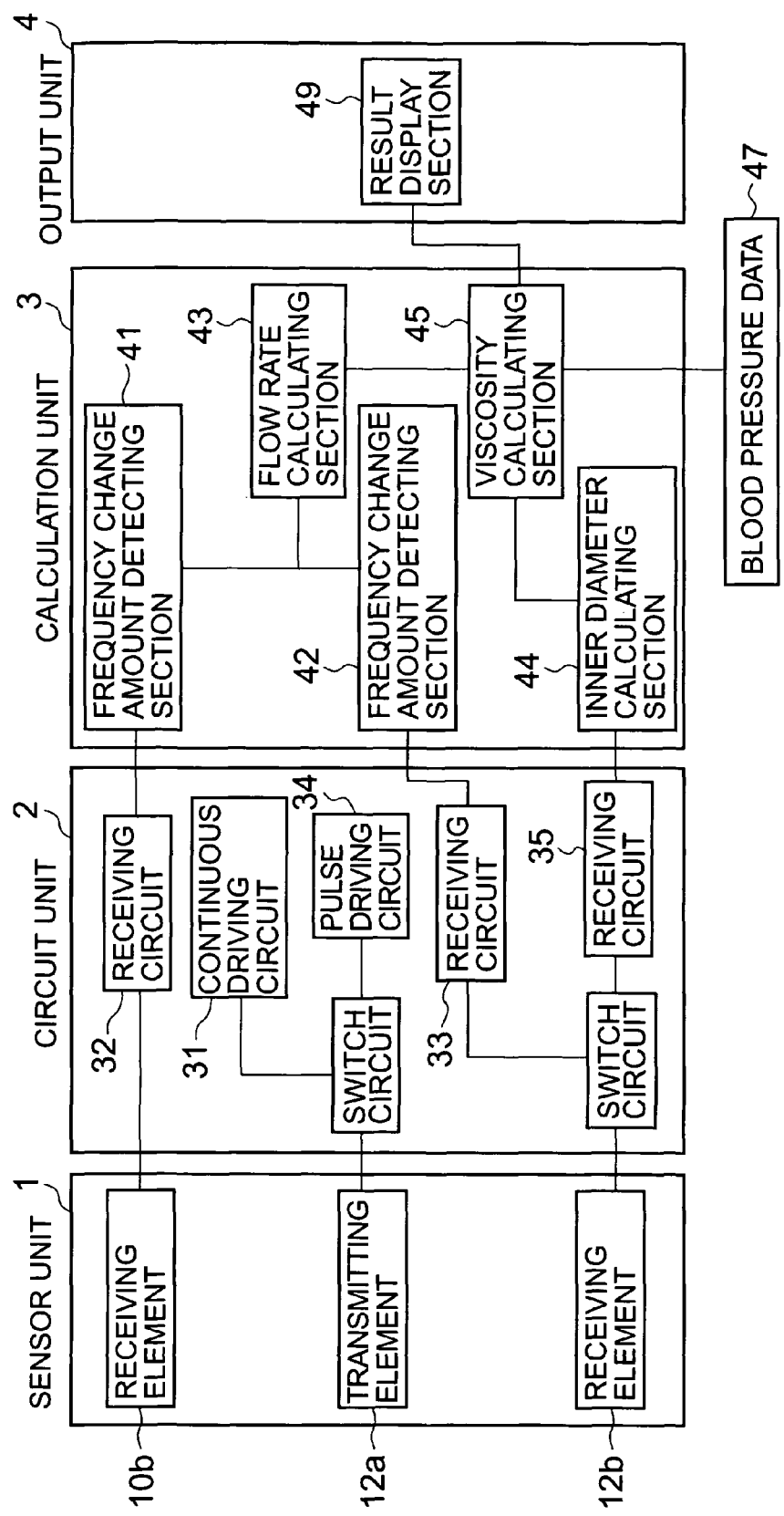
FIG. 12 is a block diagram showing a constitution of the viscosity measurement device of Modification 2.

Next, there will be described a system constitution of the blood viscosity measurement device of Modification 2 with reference to a block diagram of FIG. 12.

The blood viscosity measurement device of Modification 2 is constituted of a sensor unit 1, a circuit unit 2, a calculation unit 3, and an output unit 4.

A continuous driving circuit 31 is connected to a transmitting element 12a via a switch circuit 51.

Moreover, a pulse driving circuit 34 is connected to the transmitting element 12a via the switch circuit 51.

The switch circuit 51 is a circuit which selects a circuit to drive the transmitting element 12a. The switch circuit 51 can be switched to drive the transmitting element 12a with the continuous driving circuit 31 or the pulse driving circuit 34.

Moreover, when the transmitting element 12a is driven by the continuous driving circuit 31, the continuous wave is transmitted to the living body 18. When the element is driven by the pulse driving circuit 34, the pulse wave is transmitted.

A receiving circuit 33 is connected to a receiving element 12b via a switch circuit 52, and a receiving circuit 35 is also connected to the receiving element 12b via the switch circuit 52.

The switch circuit 52 is a circuit which selects the receiving circuit to receive a reflected wave detected by the receiving element 12b. The switch circuit 52 can be switched so that the receiving circuit 33 or 35 receives the reflected wave.

The circuit unit 2 synchronously switches the switch circuits 51 and 52. When the transmitting element 12a is driven by the continuous driving circuit 31, the receiving element 12b is connected to the receiving circuit 33. When the transmitting element 12a is driven by the pulse driving circuit 34, the receiving element 12b is connected to the receiving circuit 35.

Therefore, when the transmitting element 12a transmits the continuous wave, the continuous wave received by the receiving element 10b is output to a frequency change amount detecting section 41 via the receiving circuit 32. On the other hand, the reflected continuous wave received by the receiving element 12b is output to a frequency change amount detecting section 42 via the receiving circuit 33. Accordingly, the flow rate of the blood is calculated.

Moreover, when the transmitting element 12a transmits the pulse wave, a reflected pulse wave is received by the receiving element 12b, and output to an inner diameter calculating section 44 via the receiving circuit 35. Accordingly, the inner diameter of the blood vessel 20 is calculated.

In this manner, the circuit unit 2 switches the transmitting and receiving element 12 to a continuous wave mode and a pulse wave mode, and the element is used in measuring both of the flow rate of the blood and the inner diameter of the blood vessel.

Figure 13:
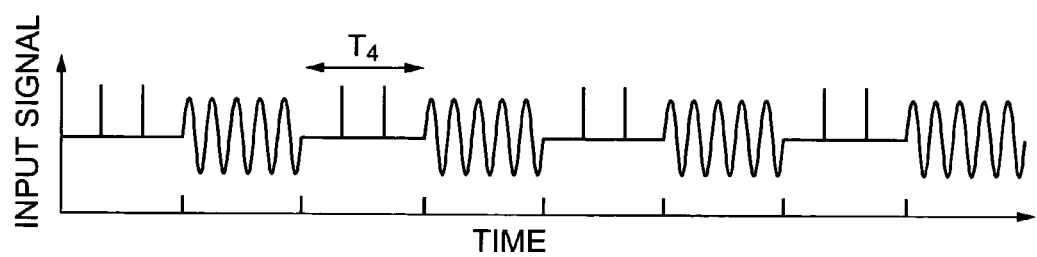
FIG. 13 is an explanatory view of switching of an ultrasonic wave mode in Modification 2.

FIG. 13 is an explanatory view of the switching of the mode of the ultrasonic wave transmitted from the transmitting and receiving element 12 during the measurement of the viscosity.

In FIG. 13, the ordinate indicates a size of an output of a transmitted wave in terms of a voltage, and the abscissa indicates time.

As shown in FIG. 13, the circuit unit 2 of Modification 2 switches the pulse wave mode and the continuous wave mode every time T4 after start of measurement, and the measurement of the flow rate of the blood and that of the inner diameter of the blood vessel 20 are alternately performed. T4 is, for example, about 0.1 [msec].

As described above, in Modification 2, while the flow rate of the blood is measured, the inner diameter of the blood vessel 20 cannot be measured. Conversely, while the inner diameter of the blood vessel 20 is measured, the flow rate of the blood cannot be measured. That is, the flow rate of the blood and the inner diameter of the blood vessel 20 cannot be measured at the same time.

However, it is not easily supposed that the flow rate of the blood and a condition of the blood vessel 20 largely change during the measurement for about ten seconds. Therefore, even when the flow rate of the blood and the inner diameter of the blood vessel 20 are alternately measured every T4, the correct viscosity can be measured.

Moreover, it is possible to omit the oscillation element 10a of Modification 1 from the sensor unit 1, and costs can be further reduced.

(Modification of Method of measuring Blood Vessel Inner Diameter)

In the above-described embodiment and Modifications 1, 2, the inner diameter of the blood vessel 20 is calculated by means of the equation (5). Here, there will be described another method of measuring the inner diameter of the blood vessel 20.

Here, the inner diameter of the blood vessel 20 is estimated utilizing the fact that the thicker the blood vessel 20 is, the more intense a reflected pulse wave becomes.

Figure 14:
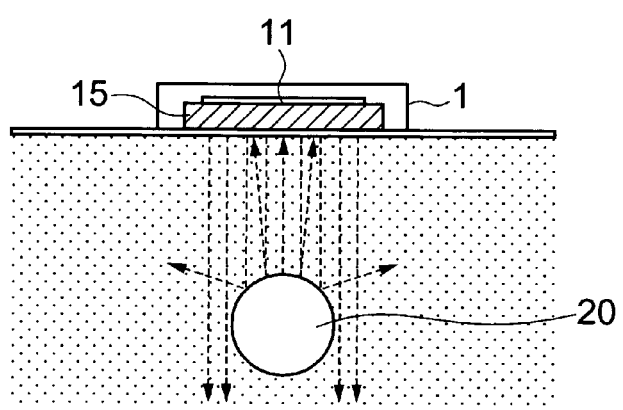
FIG. 14 is an explanatory view showing a principle in a modification of a method of measuring a blood vessel inner diameter.

FIG. 14 is a sectional view showing a sensor unit 1 of FIG. 1 viewed from the blood vessel 20.

A pulse wave transmitted from a transmitting and receiving element 11 hits the blood vessel 20, and is reflected. When an area of a portion 60 of the blood vessel 20 facing the sensor unit 1 is broader, intensity of the reflected pulse wave increases.

In general, since the blood vessel 20 has a tubular shape, the intensity of the reflected pulse wave is associated with the thickness of the blood vessel 20. When a measurement portion is specified, an individual difference of a blood vessel wall thickness is supposed to be small. Therefore, the intensity of the reflected pulse wave can be associated with the inner diameter of the blood vessel 20.

Figure 15:
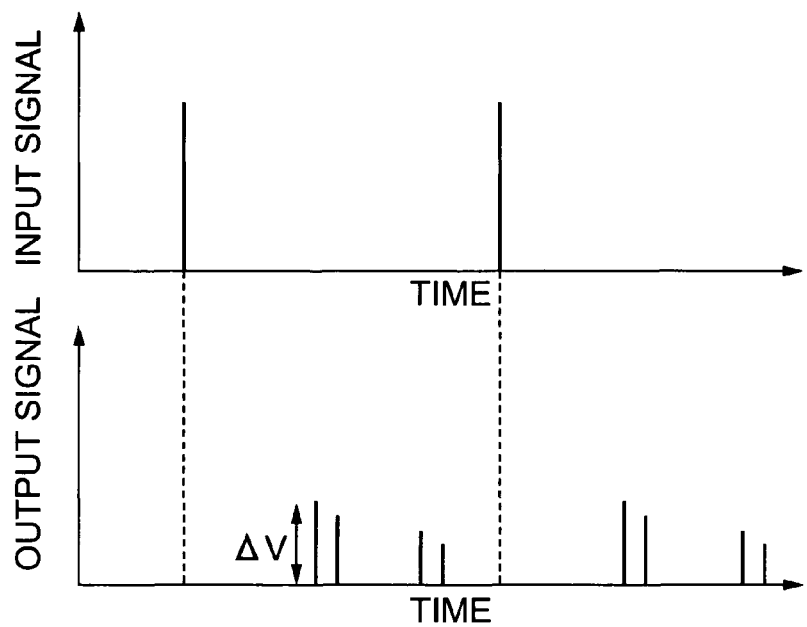
FIG. 15 is a diagram showing a reflected pulse wave in the modification of the method of measuring the blood vessel inner diameter.

In the present modification, FIG. 15A shows the pulse wave transmitted from a transmitting element 11a, and FIG. 15B shows a reflected pulse wave received by a receiving element 11b.

In either drawing, the ordinate indicates intensity in terms of a voltage, and the abscissa indicates time. Both of time axes are matched.

In FIG. 15B, ΔV denotes the intensity of the pulse wave reflected by the portion 60 of the blood vessel 20. In the present modification, the thickness of the blood vessel is obtained from ΔV.

When a relation between the intensity of the reflected pulse wave and the inner diameter of the blood vessel 20 is statistically analyzed using many samples, and organized into a database, the inner diameter of the blood vessel 20 can be estimated from the intensity of the reflected pulse wave.

It is to be noted that it is also possible to estimate the inner diameter of the blood vessel 20 by use of the pulse wave reflected by the inner wall of the blood vessel 20.

Figure 16:
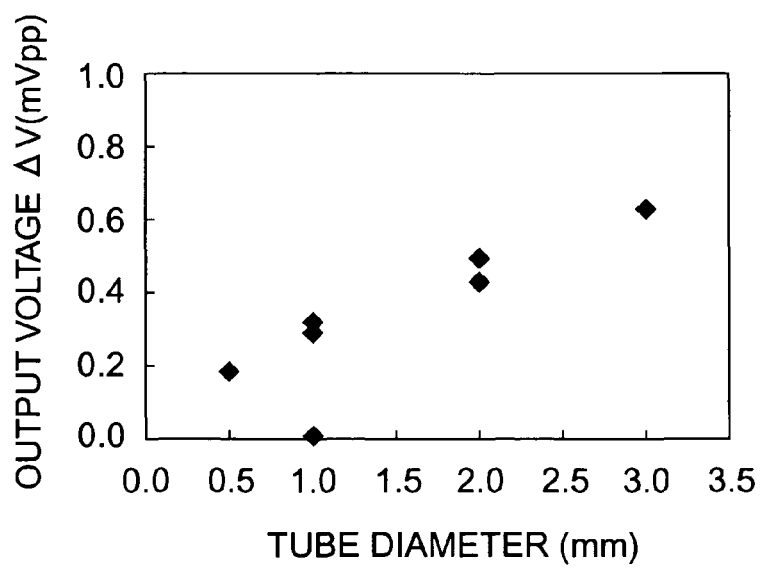
FIG. 16 is a graph showing experiment data in the modification of the method of measuring the blood vessel inner diameter.

FIG. 16 is a graph showing plotted measured voltages of pulse waves reflected by tubes submerged into water and having different thicknesses. The ordinate indicates the output voltage of the reflected pulse wave, and the abscissa indicates the tube diameter.

As shown, an output voltage of about 0.1 [mVpp] is obtained with respect to a tube having a tube diameter of 0.5 [mm], and an output voltage of about 0.3 [mVpp] is obtained with respect to a tube having a tube diameter of 1.0 [mm].

Similarly, when the tube diameter increases to 2.0 [mm] and 3.0 [mm], the output voltage of the reflected pulse wave increases.

Moreover, these data substantially linearly exist. It is therefore possible to estimate the tube diameter from the output voltage of the reflected pulse wave.

It is considered that a similar relation is established between the diameter of the blood vessel 20 and the output voltage of the reflected pulse wave, and it is possible to estimate a blood vessel diameter from the voltage of the reflected pulse wave.

What is claimed is:

1. A blood viscosity measurement device comprising:
   flow rate measurement means for measuring a flow rate of blood flowing through a blood vessel of a living body;
   inner diameter measurement means for measuring an inner diameter of the blood vessel corresponding to the measured flow rate;
   blood pressure acquiring means for acquiring a blood pressure of the blood vessel at a time different from a time when the flow rate of the blood flowing through the blood vessel and the inner diameter of the blood vessel are measured; and
   viscosity determining means for determining a viscosity of the blood flowing through the blood vessel using maximum values of the measured flow rate, the measured inner diameter, and the acquired blood pressure of the blood vessel.

2. A blood viscosity measurement device comprising:
   a flow rate measurement section that measures a flow rate of blood flowing through a blood vessel of a living body;
   an inner diameter measurement section that measures an inner diameter of the blood vessel corresponding to the measured flow rate;
   a blood pressure acquiring section that acquires a blood pressure of the blood vessel corresponding to the measured flow rate;
   a viscosity determining section that determines a viscosity of the blood flowing through the blood vessel using maximum values of the measured flow rate, the measured inner diameter, and the acquired blood pressure of the blood vessel;
   a surge transmission element that selectively transmits one of continuous waves and pulse waves from a surface of the living body into the living body; and
   a circuit unit that selectively generates the continuous waves and the pulse waves in the surge transmission element;
   wherein when the circuit unit switches between the generation of the continuous waves and the pulse waves in the surge transmission element, the surge transmission element transmits the continuous waves to be used by the flow rate measurement section and the pulse waves to be used by the inner diameter measurement section.

3. A blood viscosity measurement device comprising:
   a flow rate processing section that calculates a flow rate of blood flowing through a blood vessel of a living body;
   an inner diameter processing section that calculates an inner diameter of the blood vessel;
   a blood pressure data acquiring device that acquires blood pressure data corresponding to a blood pressure of the blood vessel; and
   a viscosity processing section that calculates a viscosity of the blood flowing through the blood vessel using a maximum values of the calculated flow rate, the calculated inner diameter, and the acquired blood pressure data;
   wherein the blood pressure data acquiring device acquires the blood pressure data separately and independently from the calculation of the flow rate of blood by the flow rate processing section and the calculation of the inner diameter of the blood vessel by the inner diameter processing section; and
   wherein the blood pressure data acquiring device acquires the blood pressure data after the flow rate processing section calculates the flow rate of the blood and the inner diameter processing section calculates the inner diameter of the blood vessel.

4. A blood viscosity measurement device comprising:
   a flow rate processing section that calculates a flow rate of blood flowing through a blood vessel of a living body in accordance with an amount of change of a frequency of a continuous ultrasonic wave transmitted to the blood flow and reflected by the blood flow;
   an inner diameter processing section that calculates an inner diameter of the blood vessel in accordance with a pulse ultrasonic wave transmitted to the blood vessel and reflected by an inner wall of the blood vessel;
   a blood pressure data acquiring device that acquires blood pressure data corresponding to a blood pressure of the blood vessel; and
   a viscosity processing section that calculates a viscosity of the blood flowing through the blood vessel using maximum values of the calculated flow rate, the calculated inner diameter, and the acquired blood pressure data.

* * * * *